United States Patent [19]

Yoshimura et al.

[11] Patent Number: 5,532,144
[45] Date of Patent: Jul. 2, 1996

[54] PROCESS FOR PREPARING HUMAN DERIVED MONOCYTE ATTRACTING PURIFIED PEPTIDE PRODUCTS USEFUL IN A METHOD OF TREATING INFECTION AND NEOPLASMS IN A HUMAN BODY

[75] Inventors: Teizo Yoshimura, Frederick; Elizabeth A. Robinson, Bethesda; Ettore Appella; Edward J. Leonard, both of Chevy Chase, all of Md.

[73] Assignee: The United States of America as represented by the Department of Health and Human Services, Washington, D.C.

[21] Appl. No.: 449,552

[22] Filed: May 24, 1995

Related U.S. Application Data

[62] Division of Ser. No. 686,264, Apr. 15, 1991, which is a continuation of Ser. No. 304,234, Jan. 31, 1989, abandoned.

[51] Int. Cl.$^6$ .................................................. C12P 21/02
[52] U.S. Cl. ............................................ 435/70.1; 514/12
[58] Field of Search .............................. 435/70.1; 514/12

[56] References Cited

U.S. PATENT DOCUMENTS 4,514,387  4/1985  Wissler .

OTHER PUBLICATIONS

S. Cushing et al., Proc. Natl. Acad. Sci. USA, vol. 87, pp. 5134–5138, Jul. 1990.
Poncz et al., Blood, vol. 69, No. 1, pp. 219–223 (Jan. 1987).
Patent Abstracts of Japan, vol. 10, No. 71, (C–334) (2128), Mar. 1986, and JP–A–60–208 921 (Teijin), Apr. 1984.
Journal of Immunol., vol. 117, No. 5, Foon et al., Part 1, Nov. 1976.
Journal of Immunol., vol. 110, No. 3, Altman et al., Mar. 1973.
Van Damme et al., J. Exp. Med., 176, pp. 59–65 (1992).
Biochemical and Biophysical Research Communications, vol. 159, No. 1, 1989, pp. 249–255.
Valente et al., "Purification of a Monocyte Chemotactic Factor . . . ", Biochemistry, vol. 27. pp. 4162–4168 (1988).
Ramb et al., "Characterization of Human Lymphocyte Derived Chemotactic Factor," Molecular Immunology, vol. 20 (3), pp. 325–332 (1983).
T. Yoshimura et al., Federation of European Biochemical Societies, vol. 244, No. 2, pp. 487–493.
T. Yoshimura et al., The Journal of Immunology, vol. 142, No. 6, pp. 1956–1962, (Mar., 1989).
D. T. Graves et al., Science, vol. 245, pp. 1490–1493.
Webster et al "Inflammation" vol. 4 No. 3 (1980) pp. 261–269.
Nakajima "Polymer Molecular Weight" Advances in Chem. Series No. 5 pp. 99–107 Erzin Estor 1973.

*Primary Examiner*—Herbert J. Lilling
*Attorney, Agent, or Firm*—Birch, Stewart, Kolasch & Birch

[57] ABSTRACT

Pure peptide products, derived from either human glioma cell line U-105MG or human peripheral blood mononuclear leukocytes are provided; the products have a molecular mass of about 8,400 daltons, and the products exhibit optimal monocyte chemotactic activity at a concentration of 1 nM. Methods of treating infection and neoplasms in a human body with the peptide products are additionally provided, as well as pharmaceutical compositions for the peptide products.

6 Claims, No Drawings

PROCESS FOR PREPARING HUMAN DERIVED MONOCYTE ATTRACTING PURIFIED PEPTIDE PRODUCTS USEFUL IN A METHOD OF TREATING INFECTION AND NEOPLASMS IN A HUMAN BODY

This application is a divisional of application Ser. No. 07/686,264, filed on Apr. 15, 1991, which is a 37 CFR §1.62 Continuation of Ser. No. 07/304,234, filed on Jan. 31, 1989 now abandoned, the entire contents of which are hereby incorporated by reference.

BACKGROUND OF THE INVENTION

Macrophages play a central role in human immune responses and defense against infection. Macrophages originate from blood monocytes, which leave the circulation in response to several signals that are thought in include chemoattractants elaborated at foci of inflammation by tissue leukocytes stimulated by invading microorganisms or by tissue injury. Heretofore, no pure, human leukocyte derived monocyte attracting substance has been provided.

SUMMARY OF THE INVENTION

The present invention is therefore primarily concerned with providing human derived, purified, peptide products that exhibit monocytic chemotactic activity (MCA). The invention is furthermore concerned with the method utilized to isolate and purify these peptide products, from human peripheral blood leukocytes and from a known human glioma cell line. The present invention is also concerned with a method of treating infection and neoplasms in a human body with the peptide products disclosed herein, and with pharmaceutical compositions for the peptide products.

The present invention provides for:

A pure peptide product which may be derived from either (a) human glioma cell line U-105MG, or (b) human peripheral blood mononuclear leukocytes; said peptide product exhibiting optimal monocyte chemotactic activity at a concentration of 1 nM; said peptide product having an estimated molecular mass of about 8,400 daltons. Human malignant glioma cell line U-105MG was deposited with the American Type Culture Collection on Dec. 28, 1988 and has been given ATCC Accession Number CRL 9932.

A pure peptide product, having a molecular mass of about 8,400 daltons, and exhibiting optimal monocyte chemotactic activity at a concentration of 1 nM, said purified peptide obtained by the process steps of:

(I) culturing live cells derived from:
  (a) human glioma cell line U-105MG, or
  (b) human peripheral blood mononuclear leukocytes, in an appropriate growth medium;

(II) separating said cells from said growth medium;

(III) chromatographing said growth medium on an Orange-A Sepharose column, utilizing an appropriate solvent, and collecting the fractions which contain the desired peptides;

(IV) chromatographing said peptide containing fractions obtained in Step III on an appropriate cation-exchange HPLC column, utilizing appropriate solvents, and collecting the fractions which contain said desired peptides;

(V) chromatographing said peptide containing fractions obtained in Step IV on a reverse phase HPLC column, utilizing an appropriate solvent, and collecting the fractions containing said desired peptides; and (VI) removing liquids from said peptide containing fractions obtained in Step V, to give said peptide product as a solid.

A method of preparing said purified peptide product, as outlined in steps I–VI above.

A pure peptide product, derived from glioma cell line U-105MG, said peptide product having an amino acid sequence of:

```
1          10        20        30
XPDAINAPVTCCYNFTNRKISVQRLASYRRITSSKCPKE
40         50        60        70
AVIFKTIVAKEICADPKQKWVQDSMDHLDKQTQTPKT
```

Wherein
  A is alanine;
  C is cysteine;
  D is aspartic acid;
  E is glutamic acid;
  F is phenylalanine;
  H is histidine;
  I is isoleucine;
  K is lysine;
  L is leucine;
  M is methionine;
  N is asparagine;
  P is proline;
  Q is glutamine;
  R is arginine;
  S is serine;
  T is threonine;
  V is valine;
  W is tryptophan;
  Y is tyrosine; and
  X is pyroglutamic acid.

A method of treating infection in a human which method comprises administering to the site of an infection in a human, an effective infection treating amount of a purified peptide product, derived from either: (a) human glioma cell line U-105MG, or (b) human peripheral blood mononuclear leukocytes; said peptide product exhibiting optimal monocytic chemotactic activity at a concentration of 1 nM; said peptide product having a molecular mass of about 8,400 daltons.

A method of treating neoplasms in a human, which method comprises administering to the site of a neoplasm in a human, an effective neoplasm treating amount of a purified peptide product, derived from either (a) human glioma cell line U-105MG, or (b) human peripheral blood mononuclear leukocytes; said peptide product exhibiting optimal monocyte chemotactic activity at a concentration of 1 nM; said peptide product having a molecular mass of about 8,400 daltons.

A pharmaceutical composition comprising:

(I) a pure peptide product, derived from either: (a) human glioma cell line U-105MG, or (b) human peripheral blood mononuclear leukocytes; said peptide product exhibiting optimal monocyte chemotactic activity at a concentration of 1 nM; said peptide product having an estimated molecular mass of about 8,400 daltons; and (II) a pharmaceutically acceptable carrier therefor.

DETAILED DESCRIPTION OF THE INVENTION

The peptide of the present invention has been purified to substantial homogeniety. Thus, the term "pure" includes peptides which have been purified from various sources by removal of contaminating human proteins and other materials as well as peptides which have been synthesized or produced in a substantially pure state by other methods. Preferably, the peptide of the present invention is at least 98% free of other proteins and peptides.

The term "Glioma cell line U-105MG" refers to a human derived cell line initiated by Pouten, J., and MacIntyre, E., "Long term culture of normal and neoplastic gliomas", *Acta Pathol Microbiol Scand.*, Vol. 74, p. 465 (1968). The cell line has been deposited with the American Type Culture Collection in Rockville, Md. in accordance with the Budapest Treaty on deposits as Deposit No. CRL 9932.

The terms "GDCF-1" and "GDCF-2" as used herein mean glioma derived chemotactic factors 1 and 2.

The terms "LDCF-1" and "LDCF-2" as used herein mean leukocyte derived chemotactic factors 1 and 2.

The term "MCA" as used herein refers to monocyte chemotactic activity as determined by an in vitro assay in a multiwell chemotaxis chamber.

The terms "Unit of monocyte chemotactic activity" means the reciprocal of dilution causing 50% of the maximal chemotactic response.

The term "nM" as used herein means nanomole, i.e., $10^{-9}$ mole.

The term "MNL" as used herein means mononuclear leukocyte.

The term "PHA" as used herein means phytohemagglutin.

The term "appropriate growth medium" as used herein includes RPMI 1640 medium containing 10% fetal calf serum.

The term "appropriate solvent" as used herein refers to aqueous solutions of alkali earth metal salts, such as sodium chloride and the like when used in conjunction with chromatographing on an Orange-A Sepharose column and cation-exchange HPLC columns; and to organic solvent mixtures for use with reverse phase HPLC columns.

The term "pharmaceutically acceptable carrier" as used herein refers to conventional pharmaceutic excipients or additives used in the pharmaceutical manufacturing art, and necessarily includes while not limited to, those excipients or additives contained herein under the caption "Pharmaceutical Compositions".

The following Examples serve to illustrate the present invention, but should not be construed to limit the invention encompassed herein.

EXAMPLE I

PURIFICATION OF MONOCYTE ATTRACTING PEPTIDES FROM HUMAN GLIOMA CELL LINE U-105MG

Materials and Methods

Cell Culture

Human glioma cell line U-105MG was utilized. Cells were cultured in 150 cm$^2$ tissue culture flasks (Costar, Cambridge, Mass.) in RPMI 1640 medium (Advanced Biotechnologies Inc., Silver Spring, Md.) supplemented with 10% fetal bovine serum (FBS, HyClone, Logan, Utah), 20mM L-glutamine and 50 µg/ml gentamycin. When cells became confluent, medium was replaced with 100 ml of FBS-free RPMI 1640 medium, which was collected 4 days later and frozen at −20° C.

Dye-ligand Chromatography

Four liters of above obtained cultured fluid were concentrated to 50 ml on a 150 mm diameter Amicon Diaflo membrane (YM-5, molecular weight cutoff 5,000), dialyzed against 20 mM tris-HCl, pH 8.0, and applied on a column of Orange-A Sepharose (1×5 cm, Amicon Corp., Danvers, Mass.) that was equilibrated with the same buffer. The column was eluted with a linear NaCl gradient (limit 0.6M) at a flow rate of 0.5 ml/min; 2 ml fractions were collected, and those with chemotactic activity were pooled.

Cation Exchange HPLC

The pool of active fractions eluted from Orange-A Sepharose was concentrated to 2 ml, dialyzed overnight at 4° C. against starting buffer (20 mM Mops, pH 6.5, in 0.1M NaCl) and applied to a 0.75×7.5 cm CM 3SW column (Toyo Soda, Tokyo) at room temperature. The column was eluted with a series of linear NaCl gradients (limit 20 mM Mops, pH 6.5, in 0.4M NaCl) at a flow rate of 1 ml/min. One ml fractions were collected and assayed for chemotactic activity. Two separate peaks were found.

Reverse Phase HPLC

Each of the active peaks from the cation exchange column was applied to a 0.5×25 cm Hi-Pore reverse phase column (BioRad, Richmond, Calif.), equilibrated with a starting solvent of 0.1% trifluoroacetic acid (TFA) in water. A linear gradient was programmed, with a limit buffer of 70% (v/v) acetonitrile in water containing 0.1% TFA. Flow rate was 1 ml/min; 1.0 ml fractions were collected, and those in the region of $A_{280}$ peaks were assayed for chemotactic activity.

RESULTS

GLIOMA CELL LINE U-105MG DERIVED PEPTIDES (GDCF-1 AND GDCF-2)

Four liters of conditioned medium from U-105MG cells were concentrated to 50 ml, dialyzed against starting buffer and applied to an Orange-A Sepharose column. The column was eluted with a linear NaCl gradient. The bulk of the protein did not bind to the column, and emerged directly in the first 27 fractions. Chemotactic activity bound to the column and was eluted between 0.2M and 0.45M NaCl. As shown in Table 1, MCA was separated from about 98% of the conditioned medium protein, and recovery of chemotactic activity was 78%. Pooled active fractions were concentrated to 2 ml and applied to a CM-HPLC column. Chemotactic activity was recovered in two separate peaks that coeluted with two major $A_{280}$ peaks. Sequential fractions corresponding to the two MCA peaks were analyzed by SDS-PAGE. The first MCA peak (GDCF-1), which had maximal chemotactic activity in fractions 36 and 37, showed a major band with maximal intensity in these fractions. There was also a narrower band immediately about the major band, which could be seen in the lanes of fractions 35 and 36. The second MCA peak (GDCF-2), with maximal chemotactic activity in fractions 45 and 46, showed a single major band with peak intensity in these fractions. By reference to the mobility of protein standards, estimates of the molecular masses of GDCF-1 and -2 were 15 kDa and 13 kDa. For further purification, GDCF-1 (fraction 37) and GDCF-2 (fractions 45 and 46) were applied to reverse phase HPLC columns and eluted with a linear acetonitrile gradient.

Each MCA peak coeluted with a single, sharp, $A_{280}$ peak. The presence, in the chromatograms of absorbance peaks without chemotactic activity showed that the reverse phase column removed residual extraneous protein. This is also shown in Table 1 by the increased specific activity 6f the RP-HPLC products. When RP-HPLC GDCF-1 and GDCF-2 were analyzed by SDS-PAGE, single bands were found, with estimated molecular masses of 15 kDa and 13 kDa, respectively. As summarized in Table 1, from 4 liters of conditioned medium, about 5 μg of GDCF-1 and 19 μg of GDCF-2 were purified to apparent homogeneity. Specific activity was 165 times that of the starting material for GDCF-1, and 150 times for GDCF-2. Total recovery was approximately 13%.

Amino Acid Analysis of GDCF-1 and GDCF-2

Table 2 shows the amino acid composition of purified GDCF-1 and -2, based on two separate analyses of each peptide. Within the limits of error of the method, the amino acid composition of the peptides is identical. A minimal molecular mass, calculated from the amino acid composition, is approximately 8400 daltons.

When N-terminal amino acid analysis was attempted, no degradation of either peptide occurred, suggesting that the N-terminus was blocked.

Assay of GDCF Chemotactic Activity for Monocytes and Neutroohils

For both peptides, about 35% of monocytes added to assay wells migrated at the optimal concentration of 1 nM. No significant neutrophil migration was observed over a GDCF concentration range of 0.01 to 30 nM in that experiment. Thus, showing GDCF attracts monocytes but not neutrophils.

Assay to Distinguish Chemotaxis from Chemokinesis

Purified GDCF was added in different concentrations to top and bottom wells of multiwell chambers, as outlined in Table 3. Dose-dependent monocyte migration was observed only when GDCF was in bottom wells;. No significant migration occurred when top and bottom wells contained equal concentrations of GDCF, showing that migration was due primarily to chemotaxis, not chemokinesis.

DISCUSSION OF RESULTS

Two chemotactic peptides for human monocytes, GDCF-1 and GDCF-2, were purified to apparent homogeneity from culture fluid of a human glioma cell line. Although these two peptides were separated into two completely distinct peaks by CM-HPLC chromatography, their elution patterns from a reverse phase HPLC column were identical; and their amino acid compositions were indistinguishable. Chemotactic potency and efficacy of both peptides were very similar (Table III); and both were chemotactic for monocytes but not neutrophils. It is possible that the two peptides differ only by post-translation modifications, such as phosphorylation, glycosylation or degradation. Based on the amino acid composition, our estimate of the molecular mass of GDCF is 8400 daltons, which is considerably less than the 15 and 13 kDa values determined by SDS-PAGE for GDCF-1 and -2. Discrepancies between molecular mass estimates obtained by these different methods of biologically active peptides have been reported by others, e.g., Richmond, A., et al., *Embo. J.*, Vol. 7, p. 2025-33 (1988).

As shown in the last column of Table 2, purification of GDCF to homogeneity was associated with only a 150-fold increase in specific activity, which reflects the relatively high concentration of GDCF in U-105MG glioma cell culture fluid. This is due to the absence of fetal bovine serum in the medium, and also indicates that GDCF represents a significant percentage of the proteins secreted by the U-105MG cell line.

The amino acid composition of GDCF is- different from other cytokines that have been reported to be chemotactic for monocytes including IL-1, TNF, GM-CSF, M-CSF and TGF-beta. GDCF is also distinct from other cytokines produced by glioma cells, including IL-1 and platelet-derived growth factor.

SUMMARY OF RESULTS

Two chemoattractants for human monocytes were purified to apparent homogeneity from the culture supernatant of a glioma cell line (U-105MG) by sequential chromatography on Orange-A Sepharose, an HPLC cation exchanger and a reverse phase HPLC column. On SDS-PAGE gels under reducing or non-reducing conditions, the molecular masses of the two peptides (GDCF-1 and GDCF-2) were 15 and 13 kDa, respectively. Amino acid composition of these molecules was almost identical, and differed from other cytokines that have been reported. The N-terminus of each peptide was apparently blocked. When tested for chemotactic efficacy, the peptides attracted approximately 30% of the monocytes added to chemotaxis chambers, at the optimal concentration of $10^{-9}$ gM. The activity was chemotactic rather than chemokinetic. In contrast to their interaction with human monocytes, the pure peptides did not attract neutrophils.

EXAMPLE II

PURIFICATION OF MONOCYTE ATTRACTING PEPTIDES FROM HUMAN PERIPHERAL BLOOD LEUKOCYTES:

Cell Culture

Human peripheral blood mononuclear leukocytes (MNL's) were isolated by metrizoate/Ficoll (Accurate Chemical and Scientific Corp., Westbury, N.Y.) density sedimentation of leukapheresis preparations obtained by the Blood Bank, Clinical Center, NIH, from healthy human donors. Cells were washed three times with isotonic phosphate buffered saline and resuspended in RPMI 1640 culture medium (Advanced Biotechnologies, Inc., Silver Spring, Md.) supplemented with 2 mM glutamine and 50 μg/ml gentamycin. Cells were cultured at a concentration of $5 \times 10^6$ cells per ml in tissue culture flasks with 2.5 μg/ml phytohemagglutin (PHA) (Sigma, St. Louis, Mo.). After incubation for 24 to 40 hrs, cells were harvested; cell-free conditioned medium was obtained by centrifugation at 400×g for 10 min.

Dye-ligand Affinity Chromatography

For large scale purification, 4 liters of PHA culture supernatant were concentrated to about 40 ml on a 150 mm diameter Amicon Diaflo YM-5 membrane (m.w. cutoff 5000), dialyzed against 20 mM tris-HCl, pH 8.0, and applied on a 1×5 cm column of Orange-A Sepharose (Amicon Corp., Danvers, Mass.) equilibrated with the same buffer. The column was eluted at a flow rate of 0.5 ml/min with a linear NaCl gradient to a limit of 0.6M in the same buffer. Fractions were collected and analyzed for monocytic chemotactic activity—thus indicating presence of a desired peptide.

High Pressure Liquid Chromatography Gel Filtration

Fractions containing peptides from the previous step were utilized, and HPLC gel filtration was performed at room temperature on a 7.5×600 mm TSK-2000 column (Toyo Soda, Tokyo, Japan), equilibrated with phosphate buffered saline, pH 7.4. Fractions of 0.5 ml were collected at a flow rate of 1 ml/min. The column was calibrated with bovine serum albumin (BSA), ovalbumin (OVA), chymotrypsinogen A, cytochrome c, and aprotinin. Fractions were collected and analyzed for MCA properties.

HPLC Chromatofocusing

Chromatofocusing was performed on a Mono P HR5/20 FPLC column (Pharmacia LKB Biotechnology Inc., Piscataway, N.J.). Two pH ranges were chosen, pH 7–4 and 9–6. For the 7–4 pH gradient, starting buffer was 25 mM bis-tris, pH 7.1, and the column was eluted with 10% (v/v) Polybuffer 74, pH 4.0. For pH range 9–6, 25 mM diethanolamine, pH 9.5, and 10% (v/v) Polybuffer 96, pH 6.0 were used. MCA obtained from 8 gel filtration runs on TSK-2000 was concentrated to 5 ml, and a 2 ml aliquot was dialyzed against starting buffer in a 3,500 mw cutoff dialysis bag (Spectrum Medical Industries Inc., Los Angeles, Calif.) and applied on a Mono P column. The column was eluted at a flow rate of 1 ml/min. Two ml fractions were collected; pH and chemotactic activity were determined.

Cation Exchange HPLC

The pool of fractions with chemotactic activity eluted from Orange-A Sepharose was concentrated and dialyzed against starting buffer (20 mM Mops, p 6.5, 0.1M NaCl), and applied on a 0.75×7.5 cm CM-3SW-column (Toyo Soda, Tokyo) at room temperature. The limit buffer was 20 mM Mops, pH 6.5, 0.4M NaCl. A series of linear gradients was programmed at a flow rate of 1.0 ml/min; 1.0 ml fractions were collected.

Reverse Phase HPLC

The pool of fractions eluted from the cation exchange column was applied to a 0.5×25 cm Hi-Pore reverse phase column (Bio-Rad, Richmond, Cailf.) equilibrated with a starting solvent of 0.1% trifluoroacetic acid in water. A linear gradient was programmed, with a limit buffer of 70% (v/v) acetonitrile in water containing 0.1% trifluoroacetic acid. Flow rate was 1.0 ml/min; 1.0 ml fractions were collected and assayed for MCA properties.

SIDS PAGE

Electrophoresis was carried out on a vertical slab gel of 15% acrylamide with a discontinuous tris glycine buffer system. Samples, as well as a solution of molecular weight standards, were mixed with equal volumes of double strength sample buffer (20% glycerol, 6% 2-mercaptoethanol), boiled, and applied to the gel. After electrophoresis at 12 mA for 3 hrs, the gel was stained with a silver staining kit (ICN Biomedicals, Irvine, Calif.).

Amino Acid Composition and Sequence Analysis

After a 24 hr hydrolysis in 6M HCl in vacuo at 106° C. amino acid composition was determined on a Beckman System 6300 (Beckman Instruments, Fullerton, Calif.). N-terminal sequence analysis was performed on an Applied Biosystems 470A Protein Sequencer (Applied Biosystems, Foster City, Calif.).

Chemotaxis Assay

Mononuclear cells from human venous blood were separated by centrifugation on metrizoate/Ficoll and used for chemotaxis in multiwell chanters. Cell suspensions were added to upper wells of the chambers; they were separated from lower wells containing chemoattractant by a 10 μm thick polycarbonate membrane with 5 μm diameter holes. The number of monocytes that migrated through the holes to the attractant side of the membrane during a 90 min incubation was counted with an image analyzer. Results were expressed as the percentage of the input number of monocytes that migrated per well for duplicate wells. The reference chemoattractant fMet-Leu-Phe (Peninsula Laboratories, Belmont, Calif.) was dissolved in ethanol at a concentration of 1 mM and diluted for assay.

RESULTS

Molecular Sieve Chromatography on an HPLC Column

One hundred ml of culture medium harvested 40 hr after addition of PHA to human MNL's was concentrated to 2 ml, and 200 μl was injected into a TASK-2000 column. Eluted fractions were assayed for chemotactic activity at 1:10 and 1:50 dilutions. As shown in FIG. 1, several peaks of chemotactic activity were detected at 1:10 dilution. At a 1:50 dilution, a single peak was seen, which represented about 40% of total applied activity. The center of this peak corresponded to a molecular mass of 17 kDa.

HPLC Chromatofocusing

The active fractions (34–40) from 8 runs on TSK-2000 were pooled and concentrated to 5 ml. Two ml aliquots of this material were used for chromatofocusing runs on a Mono P column. When pH range 7–4 was used, two major chemotactic activity peaks were seen, one in the pass through fractions and one at an early stage of the pH gradient. At pH range 9–6, a single broad activity peak was seen at pH 9.4 to 7.8, which represented about 85% of the applied activity. After the pH gradient was completed, an additional 15% of activity was eluted by 2M NaCl in fraction 34.

Affinity Chromatography on Orange-A Sepharose

Since human glioma cell derived monocyte chemotactic factor could bind to Orange-A Sepharose, the binding capacity of the leukocyte derived factor was studied. All of the 17 kDa, high pI chemotactic activity bound to Orange-A Sepharose, and was eluted by 0.5M NaCl.

Purification of the Basic 17 kDa Chemotactic Factor

Since the 17 kDa chemotactic factor in the culture supernatant of PHA-stimulated leukocytes behaved similarly to GDCF on TSK-2000, Mono P and Orange-A Sepharose, the purification of this factor was attempted by the same procedures as those for GDCF.

Four liters of PHA culture supernatant were concentrated to about 40 ml, dialyzed against starting buffer, and applied to an Orange-A Sepharose column. About 50% of the activity passed through the column without binding. This was not due to overloading, since activity was seen in very early fractions. The bound activity was eluted by NaCl (Table IV). Active fractions (40–56) were pooled, concentrated, dialyzed, and applied to a cation exchange column for further purification. By CM-HPLC chromatography, MCA was separated into two distinct peaks which were eluted in the middle of the NaCl gradient. Each of these peaks (fraction 39+40, fraction 49+50) was further purified on a RP-HPLC column. Each MCA peak coeluted with a sharp $A_{226}$ peak (fraction 40). The behavior of this leukocyte derived chemotactic activity on Orange-A Sepharose, CM-HPLC and RP-HPLC was very similar to that of GDCF. Therefore, the two chemotactic peptides purified from glioma cells (GDCF-1 and GDCF-2) and the two chemotacticpeptides purified from PHA-stimulated MNL's (LDCF-1 and LDCF-2) were analyzed on a single SDS-PAGE gel. The migration positions of the two glioma-derived peptides were identical to the migration positions of the two MNL-derived peptides, suggesting that the chemotactic peptides from these different cell sources were identical.

Amino Acid Analysis

Table V shows that the amino acid composition of the two leukocyte-derived chemotactic peptides is almost identical.

A minimal molecular mass, calculated from the amino acid composition, is approximately 8400 daltons. Within the limits of error of the method, the amino acid composition of LDCF is identical to that previously determined for GDCF.

When N-terminal amino acid analysis was attempted, no degradation of either peptide occurred, suggesting that the N-terminus was blocked.

Comparison of Chemotactic Activity for Monocytes and Neutrophils

Both peptides induced peak responses at $10^{-9}$M, at which about 30% of input cells migrated. The magnitude of the response to the two peptides was about the same as to fMet-Leu-Phe. Over the concentration range studied, neither peptide induced chemotaxis responses by human neutrophils.

DISCUSSION OF RESULTS

Two peptides with chemotactic activity for human monocytes were purified to apparent homogeneity from PHA-stimulated MNL's. The two peptides eluted from a CM-HPLC column in different peaks, and by SDS-PAGE had molecular masses of 15 and 13 kDa. However, they had identical elution patterns by reverse phase HPLC, similar amino acid compositions, and both had an apparently blocked amino terminus. These similarities suggest that the two peptides are derived from the same gene and differ because of post-translational modifications. Such modifications might account for not only the different elution patterns of LDCF-1 and -2 on CM-HPLC, but also the discrepancy between the molecular mass estimates by SDS-PAGE and those calculated from amino acid composition, Tung, J., et al., *Biochem. Biophys. Res. Comm.*, Vol. 42, p. 1117 (1971). Similar discrepancies have been reported by others for peptides in the same size range, Richmond, et al., supra. In addition, it appears that the two derived leukocyte derived chemotactic peptide are indistinguishable from the glioma cell line U-105MG chemotactic peptides obtained herein in Example I.

EXAMPLE III

AMINO ACID SEQUENCING OF GLIOMA CELL LINE U-150MG DERIVED HUMAN LEUKOCYTE ATTRACTING PEPTIDE (GDCF-2)

Materials and Methods

Purification of GDCF. Human glioma cell-derived monocyte chemotactic factors were purified from culture fluid of U-105MG cells by sequential chromatography on an Orange-A Sepharose column, a cation exchange column and a reverse-phase column as in Example I.

Chemical Modification of GDCF-2. GDCF-2 was fully reduced and carboxymethylated with iodo[2-$^3$H]acetic acid (Amersham, 131 Ci/mol) as described by Robinson et al, *J. Biol. Chem.*, Vol. 254, p. 11418–11430 (1979). Radioactivity was measured with an Analytic 81 liquid scintillation counter; $^3$H was counted with an efficiency of 44%. Carboxymethylated GDCF was succinylated in 4M urea-0.4M bicene, pH 8.6 with a 100-fold excess (over amino groups) of succinic anhydride (Eastman).

Enzymatic Digestion and Peptide Purification.

Carboxymethylated GDCF-2 and a control peptide, Big Gastrin 1 (Sigma) with N-terminal pyroglutamic acid, were digested with calf liver pyroglutamate aminopeptidase (Boehringer-Mannheim) essentially as described by Podell, D., et al., *Biochem. Biophys. Res. Comm.*, Vol. 81, p. 176–85 (1978). Carboxymethylated GDCF-2 was digested at 37° C. in 50 mM NH$_4$HCO$_3$ with *S. aureus* protease V8 (Boehringer-.Mannheim, 1/25, w/w) for 6 h, and with endoproteinase Asp-N (Boehringer-Mannheim 1/80, w/w) for 20 hr. Carboxymethylated, succinylated GDCF-2 was digested at 25° C. with trypsin (Worthington 1/50 w/w) for 20 hr.

Each digest was subjected to automated Edman degradation (as a mixture) before fractionation by HPLC. Peptides were purified by HPLC using a Hewlett Packard 1090A Liquid Chromatograph and Ultrapore RPSC C-3 or C-8 columns (Beckman) or an Applied Biosystems Model 130A and an RP300 Aquapore column (Applied Biosystems). Solvents were 0.10% trifluoroacetic acid in water (A) and acetonitrile (B), respectively.

Amino Acid Composition and Edman Degradation. Samples were hydrolyzed in vacuo in 6N HCl at 106° C. for 224 hr and analyzed on a Beckman System 6300. Edman degradation was performed on an Applied Biosystems 470A equipped with an on-line 120A PTH analyzer. PTH carboxymethylcysteine was detected both by HPLC (eluting slightly earlier than PTH-Gln) and by measurement of radioactivity (70 dpm $^3$H/pmol Cys).

Mass Spectrometry. Mass spectra was recorded on a tandem quadrupole Fourier transform mass spectrometer constructed at the University of Virginia. Operation of this instrument has been described previously, Hunt, D., et al., *Proc. Nat. Acad. Sci. USA*, Vol. 84, p. 620–23 (1987). Methodology for sequence analysis of peptides by laser photodissociation on the Fourier transform instrument has also been reported, Brinegar, A., et al., *Proc. Nat. Acad. Sci., USA*, Vol. 85, p. 3927–31 (1988).

Samples for mass analysis on the tandem quadrupole Fourier transform instrument were prepared by dissolving lyophilized HPLC fractions in 2–10 µl of 0.1% trifluoroacetic acid. A 0.5 to 1.0 µl aliquot of these solutions (10–50 pmol of peptide) was added to 1 µl of a 1/1 mixture of monothioglycerol/glycerol on a gold-plated, stainless-steel probe tip, 2 mm in diameter. Peptides were sputtered from this liquid matrix into the gas phase for mass analysis largely in the form of (M+H)$^+$ ions by bombarding the sample matrix with 6–10 keV Cs$^+$ ion projectiles. The latter ions were generated from a cesium ion gun (Antek, Palto, Calif.) mounted directly on the ion source of the spectrometer.

Methyl Ester Formation. A standard solution of 2N HCl in methanol was prepared by adding 800 µl of acetyl chloride dropwise with stirring to 5 ml of methanol. After the solution had stood at room temperature for 5 min, 100 µl aliquots of the reagent were added to lyophilized HPLC fractions. Esterification was allowed to proceed for 2 hr at room temperature, and the solvent was then removed by lyophilization.

RESULTS

Edman degradation of GDCF-2 yielded no sequence data, indicating that the N-terminus was blocked. Digestion with pyroglutaminase did not remove the blocking group but removed pyroglutamic acid from the control peptide. GDCF-2 was then digested with endopeptidases. Sequence analysis of the products of cleavage of carboxymethylated GDCF-2 with *Staphylococcus aureus* protease V8 or carboxymethylated, succinylated GDCF-2 with trypsin established the sequence of residues 19–76 (Table VI). The cleavage at Ser-21 by protease V8 was unusual; however, the same cleavage was observed in three separate digests. The sequence analysis data are presented in Table VII.

Peptides TS1 (1–19) and SP1 (1–21) both had blocked N-termini. SP1, containing the C-terminal sequence Arg-Lys-Ile-Ser, was analyzed by mass spectrometry. A mass spectrum recorded on 20 pmol of this material showed an abundant (M+H)$^+$ ion at m/z 2454.3. Conversion of the oligopeptide to the corresponding methyl ester shifted the observed (M+H)$^+$ ion to higher mass by 56 daltons, a result consistent with the addition of methyl groups (mass 14) to two carboxymethyl Cys residues, a free C-terminus, and one acidic residue in the peptide. Sub-digestion of SP1 fragment with endo-Asp-N afforded a single large peptide, the mass spectrum of which showed an abundant (M+H)$^+$ ion at m/z 2,246.2. Loss of 208 daltons in the above subdigestion can only be explained by placing the residues, pGluPro, in positions one and two of the parent molecule. Assignment of the third residue as Asp is dictated by the specificity of the enzyme employed in the cleavage reaction. An abundant fragment ion (m/z 2,131.3) resulting from the loss of these three N-terminal residues on the mass spectrum of the parent oligopeptide provided additional support for the above assignment.

Additional sequence information at the C-terminus of the endo-Asp-N cleavage product was obtained from fragmentation observed in the mass spectrum of the product generated as a result of on-probe acetylation. In this procedure the oligopeptide sample dissolved in the thioglycerol/glycerol matrix is treated with a 3/1 methanol/acetic anhydride for 30 s and then inserted back into the mass spectrometer. The resulting mass spectrum (M+H+=2331.4) contained abundant fragment ions of the type Y" at m/z 545, 659, 760, 907, 1021, and 1184 that allowed the C-terminal sequence to be extended back from the C-terminus by an additional five residues. This established the sequence of residues Tyr-13 to Ser21.

Subdigestion of SP1 with both endo-Asp-N and chymotrypsin afforded a single large oligopeptide, the methyl ester of which afforded a mass spectrum containing an abundant ion at m/z 1342.1. This is the predicted mass of the (M+H)$^+$ ion for the peptide formed by cleavage of 8 residues from the C-terminus of the parent molecule. The complete mass spectrum of this oligopeptide is shown in FIG. 2. Fragment ions resulting from internal cleavage of the chain at Pro-8 appear at m/z 197, 298, 473,648, and 843, and allow assignment of the sequence Pro-8 to Try-13. The last four of these ions suffer partial loss of water and thus appear as doublets separated by 18 mass units. Additional 18 mass unit doublets corresponding to fragment ions of type Y" (8) (m/z 896.6/914.6, 1010.7/1028.7, 1123.9/1141.9) allow placement of three additional residues, Ile-Asn-Ala on the N-terminal side of Pro-8. The first two residues in the peptide are assigned as Asp-Ala to account for the remaining mass of the molecule (200.1 daltons) and the expected specificity of the endo-Asp-N enzyme.

The N-terminal sequence obtained by tandem mass spectrometry was subsequently confirmed in part as follows. Cleavage of $^3$H-carboxymethylated GDCF-2 with endoproteinase Asp-N yielded a 51 residue peptide containing all the radioactivity. Edman degradation of this peptide, D1, yielded a sequence corresponding to the sequence of residues 3-23 (Table VII).

DISCUSSION OF RESULTS

The complete amino acid sequence of GDCF-2 was determined by Edman degradation and tandem MS. Although the sequence of residues 19–76 was obtained with relative ease by fragmentation and Edman degradation, the sequence of the blocked N-terminal 18 residues posed a difficult problem. Pyroglutamic acid was suspected to be the N-terminal residue but digestion with pyroglutamate aminopeptidase did not deblock GDCF-2 (due to the presence of proline at position 2). Tandem MS provided the sequence of peptide SP1 (1–21) expending only picomole amounts of the peptide. In addition, partial sequence data for native GDCF-1 were obtained by this method. These data indicate that GDCF-2 and GDCF-1 are virtually identical molecules but that the N-terminus of GDCF-1 may contain an additional residue and/or a different N-terminal post-translational modification (data not shown). The four half-cystines of GDCF-1 were found to participate in two disulfide bridges, Cys-11 or Cys-12 to Cys-36 and Cys-11 or Cys-12 to Cys-52 (GDCF-2 numbering).

The molecular weight of GDCF-2, calculated from the amino acid sequence, is 8700 kDa whereas both native and carboxymethylated GDCF-2 migrate as 13 kDa species on NaDoDSO$_4$/PAGE gels. We have no explanation for this discrepancy since no post-translational modifications, other than the formation of pyroglutamic acid, were detected in the sequence analyses. A similar discrepancy between predicted and observed molecular weight was reported for the melanoma growth factor, MGSA, which consists of 73 amino acids, but migrates as a 13 kDa species, Richmond, A., et al, supra. Anomalous migrations on NaDoDSO$_4$/PAGE gels have been commonly observed for basic proteins, Tung et al., supra.

EXAMPLE IV

TREATMENT OF INFECTION IN A HUMAN

When an effective, infection treating amount of one of the purified peptide products, prepared in either Examples I or II above, is administered to a human, and to the site of an infected area in a human, control of that infection is expected. The volume of the infection treating peptide composition to be administered, and the frequency of administration will be determined by the treating physician.

EXAMPLE V

TREATMENT OF A NEOPLASM IN A HUMAN

When an effective, neoplastic treating amount of one of the purified peptide products, prepared in either Examples I or II above, is administered to a human, and to the site of a neoplasm in a human, control of the neoplasm is expected due to peptide induced accumulation of monocytes at the site. The volume of the neoplasm-treating peptide composition to be administered, and the frequency of administration will be determined by the treating physician.

EXAMPLE VI

TREATMENT OF INFLAMMATORY DISEASE WITH A PEPTIDE INHIBITOR

Since the structure of the GDCF-2 peptide provided herein is now known, it is possible to synthesize short peptides reflecting partial sequences of the complete GDCF-2 peptide. These synthesized peptides can be screened to find one that binds to the monocyte receptor site without stimulating a chemotactic response. If such a peptide is found, it can be used in clinical trials to control symptoms in human chronic inflammatory diseases that are characterized by inappropriate monocyte infiltration. The volume of the infection-treating peptide composition to be administered, and the frequency of administration will be determined by the treating physician.

TABLE I

Purification of Human GDCF

| | Total protein, mg | Total MCA, units[3] | Specific activity units/mg |
|---|---|---|---|
| Crude supernatant | 29[1] | 200,000 | 6,900 |
| Concentrated and dialyzed supernatant | 29 | 190,000 | 6,600 |
| Orange-A Sepharose CM-HPLC | 0.52[1] | 148,000 | 288,000 |
| P-I (frs 36 + 37) | 0.03[1] | 21,600 | 720,000 |
| P-II (frs 45 + 46) Reverse phase HPLC | 0.03[1] | 18,200 | 607,000 |
| GDCF-1 | 0.005[2] | 5,700 | 1,140,000 |
| GDCF-2 | 0.019[2] | 20,000 | 1,053,000 |

[1]Protein concentration was determined by dye protein assay with bovine serum albumin as standard.
[2]Protein concentration was calculated from amino acid composition.
[3]MCA concentration of 1 unit/ml was defined as the reciprocal of the dilution at which 50% of the maximal chemotactic response was obtained.

TABLE II

Amino Acid Composition of Human GDCF

| | Residues per molecule[1] | |
|---|---|---|
| Amino Acid | GDCF-1 | GDCF-2[2] |
| Asp + Asn | 7.6 | 8.0 |
| Thr | 6.8 | 6.8 |
| Ser | 4.6 | 4.6 |
| Glu + Gln | 8.4 | 8.0 |
| Pro | 5.1 | 4.5 |
| Gly | 2.0 | 0.3 |
| Ala | 5.7 | 6.1 |
| Val | 4.7 | 4.5 |
| Met | 0.9 | 0.7 |
| Ile | 5.3 | 5.0 |
| Leu | 2.3 | 2.3 |
| Tyr | 1.8 | 1.8 |
| Phe | 2.1 | 2.0 |
| His | 1.2 | 0.9 |
| Lys | 8.6 | 9.1 |
| Arg | 4.0 | 3.6 |
| Cys | ND[3] | 3.5[4] |
| Trp | ND | ND |

[1]The data were calculated on the basis of a total of 74 residual/molecule.
[2]GDCF-2 was reduced and 3H-carboxymethylated for composition analysis.
[3]ND: not determined.
[4]H-carboxymethylcysteine.

TABLE III

Assay to distinguish chemotactic from chemokinetic activity in Glioma Cell Line U-105MG Derived Purified Peptide Products

| | Concentration in bottom wells | | | |
|---|---|---|---|---|
| Concentration in top wells | 0 | $4 \times 10^{-11}$ | $2 \times 10^{-10}$ | $10^{-9}$ |
| | Monocyte migration, % of input cell number ± SEM | | | |
| A:GDCF-1 | | | | |
| 0 | 1 ± 0.2 | 5 ± 0.9 | 22 ± 2.4 | 35 ± 0.7 |

TABLE III-continued

Assay to distinguish chemotactic from chemokinetic activity in Glioma Cell Line U-105MG Derived Purified Peptide Products

| | Concentration in bottom wells | | | |
|---|---|---|---|---|
| Concentration in top wells | 0 | $4 \times 10^{-11}$ | $2 \times 10^{-10}$ | $10^{-9}$ |
| | Monocyte migration, % of input cell number ± SEM | | | |
| $4 \times 10^{-11}$ | 1 ± 0.2 | 4 ± 0.5 | 15 ± 1.3 | 34 ± 4.6 |
| $2 \times 10^{-10}$ | 2 ± 0.4 | 2 ± 0.3 | 3 ± 1.2 | 21 ± 4.2 |
| $10^{-9}$ | 1 ± 0.2 | 1 ± 0.1 | 1 ± 0.1 | 3 ± 0.2 |
| B:GDCF-2 | | | | |
| 0 | 2 ± 0.2 | 12 ± 1.8 | 25 ± 6.2 | 27 ± 3.9 |
| $4 \times 10^{-11}$ | 1 ± 0.1 | 5 ± 0.5 | 18 ± 0.6 | 26 ± 5.0 |
| $2 \times 10^{-10}$ | 3 ± 0.5 | 2 ± 0.2 | 5 ± 0.6 | 24 ± 1.5 |
| $10^{-9}$ | 1 ± 0.1 | 2 ± 0.1 | 2 ± 0.1 | 4 ± 0.1 |

TABLE IV

Amino Acid Composition of Human LDCF-1 and -2

| | Residues per molecule | |
|---|---|---|
| Amino Acid | LDCF-1 | LDCF-2 |
| Asp + Asn | 8.1 | 7.8 |
| Thr | 6.4 | 6.7 |
| Ser | 5.6 | 4.7 |
| Glu + Gln | 9.4 | 8.9 |
| Pro | 5.4 | 5.2 |
| Gly | 2.2 | 3.2 |
| Ala | 6.2 | 6.0 |
| Val | 4.8 | 4.9 |
| Met | 0.7 | 0.9 |
| Ile | 4.8 | 5.2 |
| Leu | 2.4 | 2.3 |
| Tyr | 1.6 | 1.5 |
| Phe | 1.9 | 2.1 |
| His | 1.2 | 1.2 |
| Lys | 8.0 | 8.4 |
| Arg | 3.7 | 3.7 |
| Cys | ND[a] | ND |
| Trp | ND | ND |

[a]ND: not determined.

TABLE V

Purification of Monocyte Chemotactic Peptides

| | Total protein, mg | Total MCA, units[c] | Specific activity units/mg |
|---|---|---|---|
| Crude supernatant | 79[a] | 300,000 | 3,800 |
| Concentrated and dialyzed supernatant Orange-A Sepharose | 57[a] | 162,000 | 2,800 |
| Pass-through | 55[a] | 89,000 | 1,600 |
| Bound CM-HPLC | 1.7[a] | 106,000 | 62,000 |
| P-I | 0.10[a] | 30,000 | 300,000 |
| P-II RP-HPLC | 0.28[a] | 16,000 | 57,000 |
| LDCF-1 | 0.042[b] | 20,000 | 480,000 |
| LDCF-2 | 0.020[b] | 10,000 | 500,000 |

[a]Protein concentration was determined by dye protein assay with bovine serum albumin as standard.
[b]Protein concentration was calculated from amino acid composition.

TABLE V-continued

Purification of Monocyte Chemotactic Peptides

| | Total protein, mg | Total MCA, units[c] | Specific activity units/mg |
|---|---|---|---|

[c]Chemotactic activity of 1 unit/ml was defined as the reciprocal of the dilution at which 504 of the maximal chemotactic response was obtained.

TABLE VI

Amino Acid Sequence for GDCF-2
Amino acid sequence of GDCF-2 deduced from *S. aureus* protease V8 (SP) and aspartylendopeptidase *P. fragi* protease (D) peptides and from tryptic peptides of succinylated GDCF-2 (TS).
───── , tandem MS; ─────── , Edman degradation; ─ ─ ─ ─ ─ ─ ,
unsequenced portions of a particular peptide.

```
1               10                  20                  30
X P D A I N A P V T C C Y N F T N R K I S V Q R L A S Y R R I T S S K C P K E
|─────── SP1 ──────────|──────── SP2 ──────────|
|──────── TS1 ─────────|── TS2 ──|── TS3 ──|
        |──────────────────── D1 ────────────

40              50                  60                  70
A V I F K T I V A K E I C A D P K Q K W V Q D S M D H L D K Q T Q T P K T
|─── SP3 ────|──────── SP4 ────────────────|
     ─────────── TS4 ────────────── ─ ─ ─ ─ ─ ─ ─ ─|
─ ─ ─ ─ ─ ─ ─ ─ ─ ─ ─|
``` where:
  A is alanine;
  C is cysteine;
  D is aspartic acid;
  E is glutamic acid;
  F is phenylalanine;
  H is histidine;
  I is isoleucine;
  K is lysine;
  L is leucine;
  M is methionine;
  N is asparagine;
  P is proline;
  Q is glutamine;
  R is arginine;
  S is serine;
  T is threonine;
  V is valine;
  W is tryptophan;
  Y is tyrosine; and
  X is pyroglutamic acid.

TABLE VII

Peptide PTH Amino Acid (yield)*

| Cycle | D1 | | SP2 | | SP3 | | SP4 | | TS2 | | TS3 | | TS4 | |
|---|---|---|---|---|---|---|---|---|---|---|---|---|---|---|
| 1 | D | (27) | V | (72) | A | (1494) | I | (191) | K | (320) | L | (60) | I | (279) |
| 2 | A | (26) | Q | (84) | V | (582) | C | (185) | I | (281) | A | (124) | T | (110) |
| 3 | I | (24) | R | (23) | I | (490) | A | (168) | S | (173) | S | (102) | S | (124) |
| 4 | N | (21) | L | (60) | F | (463) | D | (123) | V | (200) | Y | (78) | S | (158) |
| 5 | A | (23) | A | (72) | K | (447) | P | (131) | Q | (130) | R | (27) | K | (76) |
| 6 | P | (24) | S | (61) | T | (228) | K | (93) | R | (68) | R | (12) | C | (62) |
| 7 | V | (11) | Y | (41) | I | (329) | Q | (101) | | | | | P | (53) |
| 8 | T | (10) | R | (34) | V | (300) | K | (81) | | | | | K | (64) |

TABLE VII-continued

Peptide
PTH Amino Acid (yield)*

| Cycle | D1 | | SP2 | | SP3 | | SP4 | | TS2 | TS3 | | TS4 | |
|---|---|---|---|---|---|---|---|---|---|---|---|---|---|
| 9  | C | (11) | R | (37) | A | (321) | W | (30) | | E | | (53) | |
| 10 | C | (12) | I | (42) | K | (285) | V | (59) | | A | | (42) | |
| 11 | Y | (12) | T | (34) | E | (143) | Q | (74) | | V | | (30) | |
| 12 | N | (12) | S | (28) |   |       | D | (56) | | I | | (34) | |
| 13 | F | (16) | S | (27) |   |       | S | (37) | | F | | (29) | |
| 14 | T | (6)  | K | (11) |   |       | M | (33) | | X | | (29) | |
| 15 | N | (8)  | C | (22) |   |       | H | (18) | | T | | (18) | |
| 16 | R | (6)  | P | (19) |   |       | L | (31) | | I | | (17) | |
| 17 | K | (2)  | K | (7)  |   |       | D | (23) | | V | | (15) | |
| 18 | I | (9)  | E | (5)  |   |       | K | (17) | | A | | (20) | |
| 19 | S | (3)  |   |      |   |       | Q | (27) | | K | | (16) | |
| 20 | V | (3)  |   |      |   |       | T | (14) | | E | | (10) | |
| 21 | Q | (8)  |   |      |   |       | Q | (19) | | I | | (10) | |
| 22 | — |      |   |      |   |       | T | (11) | | C | | (13) | |
| 23 | L | (6)  |   |      |   |       | P | (8)  | | A | | (11) | |
| 24 |   |      |   |      |   |       | K | (5)  | | D | | (7)  | |
| 25 |   |      |   |      |   |       | T | (5)  | | P | | (7)  | |
| 26 |   |      |   |      |   |       |   |      | | K | | (4)  | |
| 27 |   |      |   |      |   |       |   |      | | Q | | (4)  | |
| 28 |   |      |   |      |   |       |   |      | | K | | (1)  | |
| 29 |   |      |   |      |   |       |   |      | | W | | (2)  | |
| 30 |   |      |   |      |   |       |   |      | | V | | (2)  | |
| 31 |   |      |   |      |   |       |   |      | | Q | | (2)  | |
| 32 |   |      |   |      |   |       |   |      | | D | | (4)  | |
| 33 |   |      |   |      |   |       |   |      | | S | | (1)  | |
| 34 |   |      |   |      |   |       |   |      | | M | | (1)  | |
| 35 |   |      |   |      |   |       |   |      | | — |   |      | |
| 36 |   |      |   |      |   |       |   |      | | H | | (2)  | |
| 37 |   |      |   |      |   |       |   |      | | L | | (1)  | |

*The yield at each cycle is in pmoles. C = carboxymethylcysteine, K = succinylated lysine.

Pharmaceutical Compositions

The purified peptide products of the present invention may be made into pharmaceutical compositions by combination with appropriate pharmaceutically acceptable carriers or diluents, and may be formulated into preparations in solid, semi-solid, liquid or gaseous forms such as tablets, capsules, powders, granules, ointments, solutions, suppositories, injections, inhalants, and aerosols in the usual ways for their respective route of administration. The following methods of administration and excipients provided therewith, are merely exemplary of available methods which may be employed to deliver the purified peptide products of the present invention to the site of an antigen challenge, or a neoplasm in a human, and they should in no way be construed as limiting the present invention.

In pharmaceutical dosage forms, the compounds of the present invention may be used along or in appropriate association, as well as in combination with other pharmaceutically active compounds.

In the case of oral preparations, the peptide products of the present invention may be used alone or in combination with appropriate additives to make tablets, powders, granules or capsules, e.g., with conventional additives such as lactose, mannitol, corn starch or potato starch; with binders such as crystalline cellulose, cellulose derivatives, acacia, corn starch, potato starch or sodium carboxymethylcellulose; with lubricants such as talc or magnesium stearate; and if desired, with diluents, buffering agents, moistening agents, preservatives and flavoring agents.

Furthermore, the peptide products of the present invention may be made into suppositories by mixing with a variety of bases such as emulsifying bases or water-soluble bases.

The purified peptide products of the present invention may be formulated into preparations for injections by dissolving, suspending or emulsifying them in an aqueous or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In the cases of inhalations or aerosol preparations, the peptide of the present invention in the form of a liquid or minute powder may be filled up in an aerosol container with gas or liquid spraying agents, and if desired, together with conventional adjuvants such as humidifying agents. They may also be formulated as pharmaceuticals for non-pressurized preparations such as in a nebulizer or an atomizer.

The amount of peptide products of the present invention to be used varies according to the degree of infection or the size and type of neoplasm encountered in a human. A suitable dosage is envisioned at about 0.001–1.0 mg/kg body weight per day for treatment of infection or neoplasms in a human. The preferred dosage being that amount sufficient to effectively treat an infection or neoplasm in a human.

A method of treatment utilizing the purified peptide products of the present invention can also be had by oral ingestion of one of the peptides of the present invention with a pharmaceutically acceptable carrier.

Unit dosage forms for oral administration such as syrups, elixirs, and suspensions wherein each dosage unit, e.g., teaspoonful, tablespoonful, contains a predetermined amount of the purified peptide product of the present invention. Inclusion of pharmaceutically acceptable excipients, are readily known by those skilled in the art.

Parenteral administration of the purified peptide products of the present invention can be had by administration with a pharmaceutically acceptable carrier, such as Sterile Water for Injection, USP, or by normal saline.

The purified peptide products of the present invention can be administered rectally via a suppository. The suppository can include vehicles such as cocoa butter, carbowaxes and polyethylene glycols, which melt at body temperature, yet are solidified at room temperature.

The purified peptide products of the present invention can be utilized in aerosol formulation to be administered via inhalation. The purified peptide products can be formulated into pressurized aerosol containers together with pharmaceutically acceptable propellants, such as dichlorodifluoromethane, propane, nitrogen and the like.

The term "unit dosage form" as used herein refers to physically discrete units suitable as unitary dosages for human and animal subjects, each unit containing a predetermined quantity of a purified peptide product calculated in an amount sufficient to produce the desired effect in association with a pharmaceutically acceptable, diluent, carrier or vehicle. The specifications for the novel unit dosage forms of the present invention depend on the particular compound employed and the effect to be achieved, and the pharmacodynamics associated with each compound in the host.

It is also recognized that a skilled practitioner in the art may desire to modify the above modes of administration, in order to more effectively deliver one of the purified peptide products directly to the site of an infection or neoplasm in a human body. Such modification and direct administration of one of the purified peptides of the present invention is, however, fully comprehended herein, and encompassed by the present invention.

Furthermore, it is envisioned that an injectable pharmacological composition of the peptide products of the present invention, to be administered directly to the site of an infection or neoplasm, would contain a concentration of the peptide(s), encompassed herein, that is anticipated to cause monocyte accumulation at locally injected tissue sites of human patients. This concentration is thought to be preferably not less than $10^{-8}$M and not more than $10^{-6}$M.

Lastly, it is to be understood that the present invention is only limited by the scope of the appended claims.

What is claimed is:

1. A method of preparing a pure peptide product, that consists essentially of a peptide having a molecular weight of about 8,400 daltons, and exhibiting optimal monocyte chemotactic activity at a concentration of 1 nM; said method comprising the steps of:

(I) culturing live cells derived from:
   (a) human glioma cell line U-105MG, or
   (b) human peripheral blood mononuclear leukocytes, in a growth medium;

(II) separating said cells from said growth medium;

(III) chromatographing said growth medium on an Orange-A Sepharaose column, utilizing a solvent, and collecting fractions which contain the peptide;

(IV) chromatographing said peptide containing fractions obtained in Step III on a cation-exchange HPLC column, utilizing a solvent, and collecting the fractions which contain the peptide;

(V) chromatographing said peptide containing fractions obtained in Step IV on a reverse phase HPLC column, utilizing a solvent, and collecting the fractions containing said peptide; and (VI) removing liquids from said peptide containing fractions obtained in Step V, to give said pure peptide product in a solid form.

2. The method of claim 1, wherein the growth medium comprises RPMI 1640 medium containing 10% fetal calf serum.

3. The method of claim 1, wherein the growth medium consists essentially of RPMI 1640 medium containing 10% fetal calf serum.

4. The method of claim 1, wherein the solvent referred to in Step (III) or (IV) is an aqueous solution of an alkali earth metal salt.

5. The method of claim 1, wherein the solvent used in Step (V) is an organic solvent mixture.

6. The method of claim 4, wherein the alkali earth metal salt is sodium chloride.

* * * * *